United States Patent [19]
Hendler et al.

[11] Patent Number: 5,966,212
[45] Date of Patent: Oct. 12, 1999

[54] HIGH-SPEED, HIGH-RESOLUTION, LARGE AREA INSPECTION USING MULTIPLE OPTICAL FOURIER TRANSFORM CELLS

[75] Inventors: Lawrence Hendler, Cupertino; Michael P. C. Watts, Portola Valley; Richard A. Portune, Sunnyvale, all of Calif.

[73] Assignee: Pixel Systems, Inc., Portola Valley, Calif.

[21] Appl. No.: 08/683,790

[22] Filed: Jul. 18, 1996

[51] Int. Cl.[6] .................................................. G01N 21/88
[52] U.S. Cl. .................................. 356/239.3; 356/237.2
[58] Field of Search .............................. 356/237, 237.1, 356/237.2, 237.4, 237.5, 239.1, 239.3; 438/16

[56] References Cited

U.S. PATENT DOCUMENTS

| | | | |
|---|---|---|---|
| 4,330,775 | 5/1982 | Iwamoto et al. | 356/237.5 |
| 4,360,269 | 11/1982 | Iwamoto et al. | 356/237.5 |
| 5,463,459 | 10/1995 | Morioka et al. | 356/237 |
| 5,506,676 | 4/1996 | Hendler et al. | 356/237 |

*Primary Examiner*—Richard A. Rosenberger
*Attorney, Agent, or Firm*—Skjerven, Morrill, MacPherson, Franklin & Friel LLP; David T. Millers

[57] ABSTRACT

A system includes multiple optical Fourier transform cells which simultaneously scan a device under test. The illuminated area for each Fourier transform cell is small to provide high resolution, while the number of cells is large to cover a relatively wide area and keep inspection speed high. The advantages of optical computing performed by Fourier transform optics also keeps the inspection speed high because illuminated areas are large when compared to the resolution and Fourier transforms are linear shift invariant so that optical measurements can be performed during scanning. In one embodiment, Fourier transform cells are offset from each other perpendicular to the scan direction by less that the width of an illuminated area. This provides complete coverage during scanning of a device under test. Because the illumination for the Fourier transform is collimated, the system is insensitive to focusing errors due to fluctuations in working distance.

6 Claims, 5 Drawing Sheets

HIGH-SPEED, HIGH-RESOLUTION, LARGE AREA INSPECTION USING MULTIPLE OPTICAL FOURIER TRANSFORM CELLS

BACKGROUND OF THE INVENTION

1. Field of the Invention

This invention relates to systems and methods for using Fourier transform optics to inspect devices.

2. Description of Related Art

Inspecting substrates used in integrated circuits or flat panel displays typically relies on one of three methods: scanning the substrate with a beam that generates a signal indicating reflection, transmission, or absorption of the beam in a small portions of the substrate; imaging the substrate and analyzing the resulting image; or forming the Fourier transform of a light pattern from the substrate and analyzing the Fourier transform. For these methods, reducing the area simultaneously inspected can improve the resolution (i.e., detect smaller defects or features). For scanning, a smaller beam diameter isolates the attributes of a smaller portion of the substrate. For imaging, higher magnification increases the size of features in the image but decreases the substrate area inspected by a fixed size detector. For Fourier transform inspections, transforming a light pattern from a smaller area of the substrate reduces the area represented by the Fourier transform but makes light from a small feature a larger portion of the light in the Fourier transform and therefore more easily detectable. In all these cases, decreasing area simultaneously inspected improves resolution but decreases the speed of inspection by requiring more scans, more images, or more exposures to cover a substrate.

Fourier transform based inspection systems which scan a substrate can provide fast inspection because Fourier transform optics perform "optical computing" which separates a defect signal from a non-defect signal. Optical computing allows the area illuminated by a scan beam to be large when compared to beams used in a conventional scanning system. For example, a conventional scanning system for a substrate having a feature size of a few microns might use a beam which is a few microns in diameter. A Fourier transform inspection system for the same substrate would use a beam which is millimeters in diameter. The large beam for the Fourier transform optics encompasses repetitive features which create a characteristic spatial frequency light pattern that is transformed to a distinctive Fourier transform pattern. However, when inspecting for defects about a micron in size, the amount of light reaching the Fourier plane from a defect is typically small relative to the total amount of light reaching the Fourier plane. The small signal generated by the defect may be of the same order of magnitude as the noise associated with the non-defective signal, making defect detection difficult.

Reducing the area of illumination improves the signal-to-noise ratio by making light from a defect a larger fraction of the total light, but reducing the illuminated area also increases the number of scans required to cover the substrate. For example, changing the beam diameter from 0.15 mm to 2 mm changes the inspected area by more than a factor of fifty, and requires increasing a scan rate by a similar factor to maintain the original inspection time. This magnitude of change in scan rate is typically not achievable.

SUMMARY OF THE INVENTION

In accordance with an aspect of the invention, a system for high resolution, high speed defect detection uses multiple optical Fourier transform cells and parallel analysis for scanning large area patterned and non-patterned devices. Embodiments of the invention include multiple Fourier transform cells which form Fourier transform patterns from light transmitted through and/or reflected by a device under test. Each Fourier transform cell includes a source of collimated light that illuminates an area of a device under test and a Fourier transform lens which forms a Fourier transform of the light from the illuminated area of the device under test. The illuminated area for each Fourier transform cell is small to provide high resolution, while the number of cells can be large to cover a relatively wide area and keep inspection speeds high. A detector system measures differences between the Fourier transform patterns formed and the Fourier transform patterns expected for a defect-free device. Optical computing performed by Fourier transform optics helps keep inspection speeds high because illuminated areas are large when compared to the size of detectable defects. Additionally, scanning rates are high because the Fourier transforms are linear shift invariant allowing measurements on the fly during scanning.

The Fourier transform cells can be arranged in an array which avoids interference between neighboring cells and still provides complete coverage of a scan line width. In particular, each illuminated area in a sequence of illuminated areas is offset in a direction perpendicular to the scan direction by a distance less than the width of an illuminated area. The illuminated areas are also offset from each other along the scan direction to provide room for the Fourier transform lenses and spatial filters or separators which are typically larger than the illuminated areas. In one embodiment, a scan head includes columns of Fourier transform cells, where illuminated area for adjacent columns are offset perpendicular to scan direction by the diameter of an illuminated area and have a width determined by the width of the cells.

Illumination for individual Fourier transform cells can be separately turned on and off to stop light from Fourier transform patterns formed by adjacent cells from overlapping each other. This allows tighter packing of Fourier transform cells in a scan head. One embodiment of the invention has fewer light sources than Fourier transform cells, and light from each light source is routed to a set of associated Fourier transform cells. In this fashion, light sources are multiplexed for illumination in the Fourier transform cells.

One detector system includes a spatial filter or separator per Fourier transform cell. Each spatial filter or separator is tailored for the Fourier transform which the device under test would cause if defect-free. For example, a spatial filter can block spatial components of the Fourier transform of a defect-free device, and a spatial separator can separate various components of the Fourier transform for separate measurements. Alternative embodiments have a single photodetector per spatial filter, multiple photodetectors per spatial filter or separator, or multiple spatial filters or separators per photodetector. The number of photodetectors per spatial filter/separator depends on multiplexing used for the Fourier transform cells. The photodetectors measure spatial components which pass through the spatial filter or separator to detect variations in the Fourier transform patterns which indicate a defect. A single photodetector per Fourier transform pattern is typically sufficient to identify a defect. Multiple photodetectors per spatial separator measure multiple separate components per Fourier transform pattern to allow better characterization of defects. Photodetectors can be multiplexed or shared by Fourier transform cells so that a sequence of measurements by the photodetectors matches a sequence in which illumination in Fourier transform cells are turned on and off. In particular, a single photodetector can be associated with a set of Fourier transform cells which are associated with different light sources.

In one embodiment, each Fourier transform cell includes one source of collimated light and two Fourier transform lenses. One Fourier transform lens forms a Fourier transform of light reflected from a corresponding illuminated area of the device under test, and the other forms a Fourier transform of light transmitted through the corresponding illuminated area.

BRIEF DESCRIPTION OF THE DRAWINGS

Use of the same reference symbols in different figures indicates similar or identical items.

DETAILED DESCRIPTION OF THE PREFERRED EMBODIMENTS

An inspection system includes a scan head having multiple Fourier transform (FT) cells. Each FT cell contains Fourier transform optics which transform a small illuminated area to achieve high resolution, but the combined area illuminated by all of the FT cells is large enough to provide a wide scan line for high speed scanning. A device under test can be rapidly scanned because linear shift invariance of Fourier transforms causes a uniform and defect-free device to have a Fourier transform pattern that remains constant during scanning. Additionally, each FT cell is insensitive to fluctuations in working distance because illuminating beams are uniform plane waves. For the case of transmissive substrates, the FT cells form patterns that are independent of fluctuations in working distance.

Figure 1:
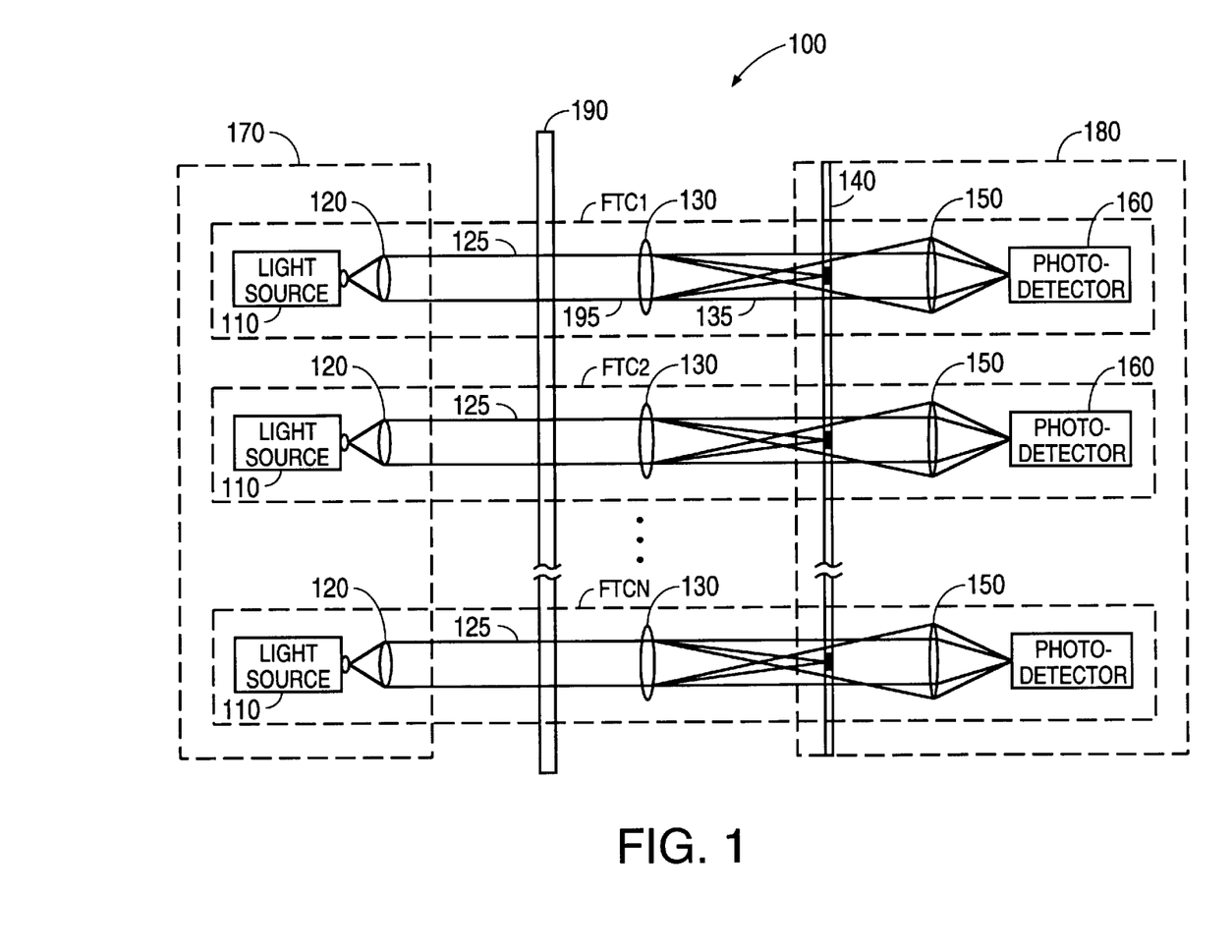
FIG. 1 shows a Fourier transform scan system in accordance with an embodiment of the invention.

FIG. 1 illustrates a Fourier transform scanning system 100 using multiple Fourier transform cells FTC1 to FTCN to inspect a device under test (DUT) 190. DUT 190 may be, for example, a portion of a flat panel display which is uniformly patterned when defect-free. Each cell FTC1 to FTCN includes: a light source 110 and a collimating lens 120 which are parts of an illuminating system 170; a Fourier transform (FT) lens 130; and a portion of a spatial filter 140, a collecting lens 150, and a photodetector 160 which are parts of a detector system 180.

For each cell FTC1 to FTCN, light source 110 generates light which collimating lens 120 collimates into a uniform intensity, parallel light beam 125. Light sources 110 are approximately point sources of light and may be, for example, individual laser diodes or optical fibers coupled to one or more lasers. Each collimating lens 120 couples to an associated light source 110 and forms light beam 125 which is aligned with the Fourier transform (FT) lens 130 associated with the light source 110. In the exemplary embodiment, parallel light beam 125 illuminates an area of DUT 190 about 0.8 mm to 2.5 mm in diameter at an intensity of about 3 mW to detect defects down to about 1 $\mu$m in size. A parallel light beam 195 which has an intensity pattern that depends on the structure of DUT 190 emerges from the illuminated area and enters a Fourier transform lens 130.

Fourier transform lenses 130 can be individual lenses, lenses of a lenslet array, individual holographic optical elements, or an array of holographic optical elements. Since light beam 195 is substantially parallel, the distance between FT lens 130 and DUT 190 is not critical to operation of system 100, and no focusing of FT lenses 130 on DUT 190 is required. Each FT lens 130 forms in the plane of spatial filter 140 a light pattern which is the Fourier transform of the intensity pattern of associated light beam 195 and is characteristic of an illuminated portion of DUT 190.

Spatial filter 140 is positioned in the Fourier plane of FT lenses 130 and includes multiple opaque patterns for simultaneous filtering of multiple Fourier transform light patterns formed by FT lenses 130. In one embodiment, spatial filter 140 has opaque regions which block light from a Fourier transform characteristic of a defect-free portion of DUT 190 so that no light passes through spatial filter 140 when the illuminated area of DUT 190 is defect-free. Alternatively, some of the light from a defect-free pattern can be transmitted or separated for measurement. Spatial filter 140 could be implemented using multiple exposures of high resolution photographic emulsion. The multiple exposures are identical opaque patterns, one for each Fourier transform cell, and can be provided all on a single plate or on multiple plates.

An alternative embodiment of the invention uses spatial separators in the Fourier plane instead of spatial filter 140. A spatial separator can, for example, be a single or multiple plate chrome on glass spatial separator. A programmable mirror array such as the Texas Instruments Digital Micromirror Device or WAH III Spatial Light Modulator can form either a spatial separator or filter. As described in U.S. Pat. No. 5,506,676 which is incorporated by reference herein in its entirety, a spatial separator allows separate analysis of different Fourier components to permit better identification of the type of defect detected. Multiple photodetectors for the various components separated from the Fourier transform pattern by a spatial separator can replace a single detector 160 shown per FT cell in FIG. 1.

The Fourier transforms are linear shift invariant so that motion of DUT 190 relative to Fourier transform cells FTC1 to FTCN does not change the Fourier transform patterns at spatial filter 140 if DUT 190 has a uniform pattern. Accordingly, inspection can continue during a continuous scanning process. If a defect enters an illuminated area of DUT 190, the associated Fourier transform pattern changes, and total amount of light passing through spatial filter 140 changes.

Collecting optics 150 collect light that passes through spatial filter 140 for measurement by detectors 160. Collecting optics 150 can be a lenslet array, holographic optical elements, or individual collecting lenses. Detectors 160 can be individual silicon photodiodes, one for each FT cell FTC1 to FTCN in FIG. 1. In one embodiment, detectors 160 are pixels of a charge coupled device (CCD) line array with optical fibers connecting each pixel to a collecting lens 150.

Alternatively, optical fibers collect and transmit light from cells to detectors with multiple cells per detector, and light sources for cells FTC1 to FTCN are separately turned on and off to identify which cell is the source of any light detected. In a similar variation of scanning system 100, light sources 110 are replaced by fewer than one light source per cell, and each light source is fiber coupled to collimating lenses 120 in multiple cells.

The scanning method used when inspecting DUT 190 depends on the arrangement and coverage of light beams 125. If the Fourier transform cells FTC1 to FTCN are arranged in line perpendicular to a scan direction, there will be gaps between illuminated areas because Fourier transform lenses 130, mountings, and the Fourier transform light patterns are wider than the beam diameter. To cover these gaps during inspection, Fourier transform cells FTC1 to FTCN are indexed (or moved perpendicular to the scan direction) in small steps (the width of an individual beam 125 after a scanning pass). This provides an interleaved scanning where a Fourier transform cell can scan a strip between strips previously scanned. Interleaved scanning continues until the gaps are covered, and then a scan head is indexed by the width of the scan head for further interleaved scanning if necessary to cover DUT 190. Alternatively, Fourier transform cells FTC1 to FTCN are arranged to cover the width of a scan line without gaps. If the accumulated width of illumination covers the width of DUT 190, a single pass scan is sufficient to inspect DUT 190. Otherwise, multiple passes are required. Each pass covers a scan line of DUT 190 along a scanning direction. In these cases, indexing moves the scan head perpendicular to the scan direction by the width of the scan line. Interleaved and conventional scanning can be back and forth along the scan direction or in typewriter-fashion returning to the same edge before beginning to scan another line. Mechanisms for implementing the necessary scanning motions are known. In alternative embodiments, one or more precision stages (not shown) move DUT 190 while FT cells FTC1 to FTCN are fixed, move FT cells FTC1 to FTCN while DUT 190 is fixed, or move both FT cells and DUT 190 simultaneously. If desired, one stage can move DUT 190 or cells FTC1 to FTCN along the scanning direction, and another stage can move cells FTC1 to FTCN or DUT 190 perpendicular to the scanning direction for indexing.

Figure 2:
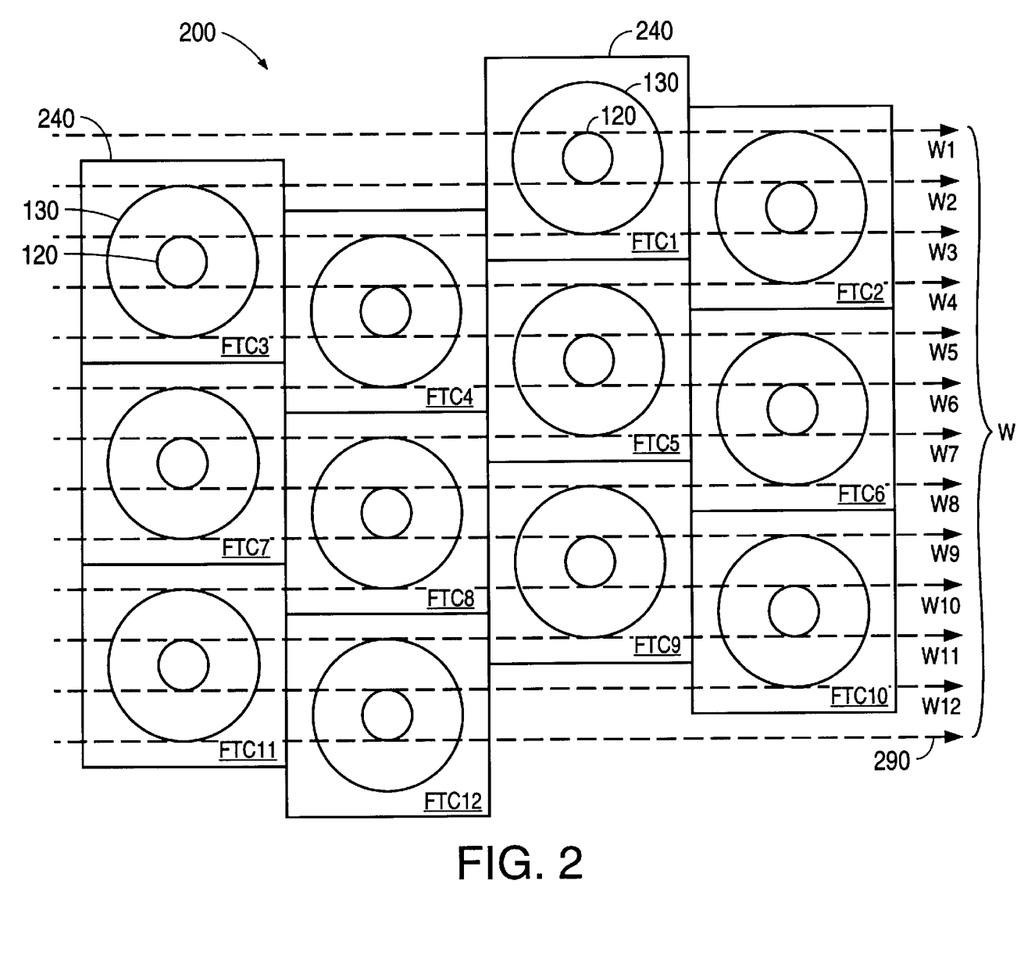
FIG. 2 shows a view of the system of FIG. 1 along an optical axis, of Fourier transform optics.

FIG. 2 shows an exemplary embodiment of a scan head 200 viewed along the optical axis of collimating lenses 120 and FT lenses 130. Areas 240 define the extent of cells FTC1 to FTC12, and each area is of sufficient size to encompass a Fourier transform light pattern formed by the corresponding FT lens 130, and mountings for associated collimating lens 120 and FT lens 130. Collection optics 150 and detectors 160 are omitted from FIG. 2 to simplify the figure. DUT 190, which is not shown in FIG. 2, would typically be between collimating lenses 120 and Fourier transform lenses 130. However, Fourier transform lenses could also be on the same side of DUT 190 as collimating lenses 120 and still provide an operable scanning system.

Scan head 200 includes twelve FT cells FTC1 to FTC12 arranged in multiple columns of FT cells. Spacing of cells FTC1 to FTC12 is determined by the diameter of the illuminating beams, and selected so that scanning DUT 190 along a scan direction 290 inspects a strip of DUT 190 having a width W without gaps. To provide complete coverage of width W, each column of FT cells is offset relative to adjacent columns by an amount less than or equal to the diameter of the collimated beams and enough columns of cells are provided so that the accumulated offset of the columns is equal to width of one of areas 240. For scan head 200, each column is offset by the diameter of a collimated beam, which for the example shown in FIG. 2 is one quarter the width of area 240 for a cell, so that four columns are required. The width of area 240 depends on the size of the Fourier transform pattern, the size of optics (collimating lens 120, FT lens 130, and collecting lens 150), and the mounts which hold the various elements. The desired width to be scanned determines the number of cells required per column.

Various other arrangements of Fourier transform cells can also provide complete coverage of scan line width W. More generally, Fourier transform cells FTC1 to FTC12 have corresponding individual scan widths W1 to W12. To completely cover width W, scan widths W1 to W12 must either overlap each other or directly adjoin each other. Offsetting each FT cell FTC1 to FTC12 in a direction perpendicular to the scan direction by a distance less than or equal to the widths W1 to W12 provides complete coverage. Offsets along the scan direction provide necessary space for optics 120 and 130 but can otherwise be selected arbitrarily. For example, a diagonal arrangement, where each cell is offset from a preceding cell by the width of an illuminated area perpendicular to the scan direction and by the width of area 240 along the scan direction, also provides complete coverage of a scan line. Scan head 200 provides a compact arrangement of Fourier transform cells FTC1 to FTC12.

Not all of FT cells FTC1 to FTC12 need to operate simultaneously. In particular, light sources 110 in FT cells FTC1 to FTC12 can be turned on and off in a pattern which avoids simultaneous measurements by adjacent cells. In this way, the Fourier pattern or stray light from one cell can extend into areas 240 of adjacent cells without interfering with measurements by the adjacent cells. Areas 240 can therefore be smaller than otherwise possible. Switching illumination on and off is performed quickly relative to the scanning speed so that turning off some cells for short periods of time does not affect coverage of an inspection.

Figure 3:
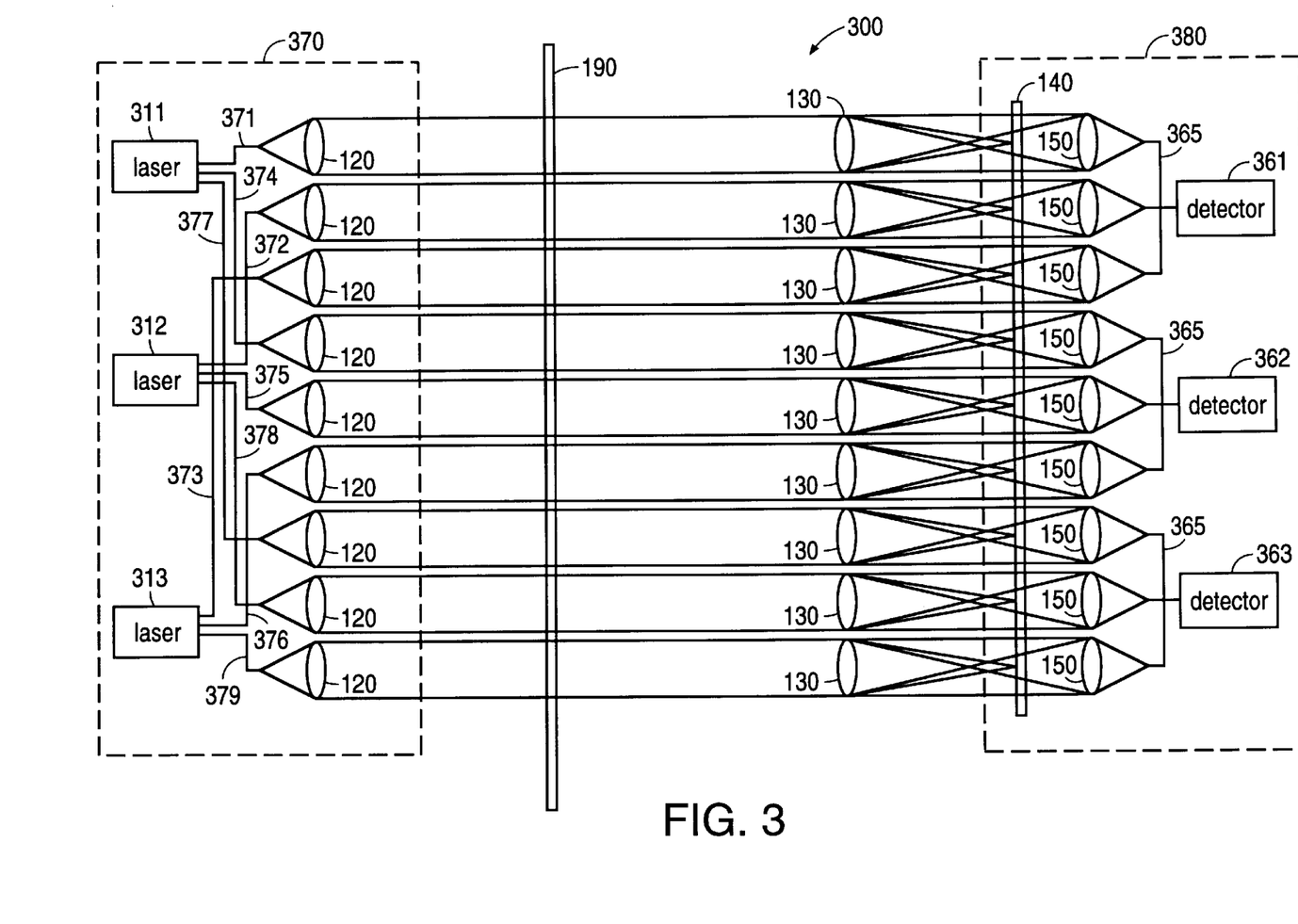
FIG. 3 illustrates Fourier transform cells in a system using multiplexed light sources and detectors.

FIG. 3 shows a system 300 having a multiplexed illumination system 370 for a column of Fourier transform cells arranged as shown in FIG. 2. In the embodiment of FIG. 3, illumination system 370 has three light sources 311 to 313 for nine cells, and only one of the three light sources 311 to 313 operates at a time. Light source 311 provides light through optical fibers 371, 374, and 377 to the first, fourth, and seventh FT cells in the column. Light source 312 provides light through optical fibers 372, 375, and 378 to the second, fifth, and eighth FT cells in the column. Light source 313 provides light through optical fibers 373, 376, and 379. With only one of light sources 311 to 313 operating at a time no two adjacent FT lenses 130 form a Fourier transform light pattern, and only one FT lens in each set of three adjacent FT lenses form a Fourier transform light pattern. Accordingly, one of collecting lenses 150 collects most or all of the light passing through filter 140. A detector system 380 has only three photodetectors 361 to 363 for the nine FT cells in the column. Photodetectors 361, 362, and 363 respectively connect through optical fibers 365 to collecting lenses 150 for the first, second, and third set of three FT cells in the column. Each detector 361 to 363 measures light for only one FT cell at a time because illumination system 370 only illuminates one cell in each of the first, second, and third sets of three FT cells in the column. Other columns in an array could have similar illumination systems.

In an embodiment of the invention where Fourier transform cells are arranged as shown in FIG. 2, a multiplexed illumination system having three light sources and a detection system having four photodetectors (one for each column) could prevent simultaneous operation of adjacent cells during scanning. In an exemplary embodiment, a first light source provides simultaneous illumination for Fourier transform cells FTC1, FTC3, FTC6, and FTC8; a second light source provides simultaneous illumination for cells FTC5, FTC7, FTC10, and FTC12; and a third light source provides simultaneous illumination for cells FTC2, FTC4, FTC9, and FTC11. The three light sources are operated in sequence so that no two adjacent Fourier transform cells are simultaneously illuminated. Only one FT cell per column operates at a time so that each detector measures light for one FT cell at a time. The exemplary system has low cost because only three light sources and four detectors are required for twelve cells and has low light noise between cells because adjacent cells do not operate simultaneously.

The multiplexing illumination in other embodiments of the invention will depend on the number and arrangement of the Fourier transform cells and the number of independent light sources. The frequency at which cells are turned on and off depends upon the scan speed, the speed of the detectors, and the speed of analyzers which process signals from the detectors. The frequency should be high enough that an FT cell forms a first illuminated area that overlaps a second illuminated area formed by the FT cell enough to provide complete scan coverage.

Figure 4A:
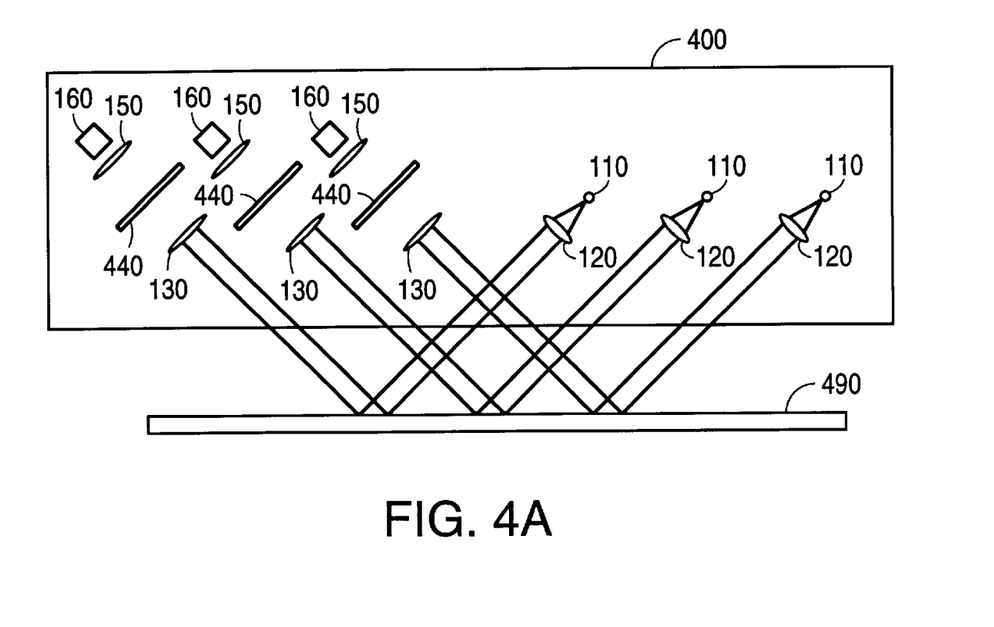
FIG. 4A shows a Fourier transform scanning system for inspecting reflective devices in accordance with an embodiment of the invention.

FT scanning systems 100 and 300 inspect a DUT 190 which transmits light. A scan head 400 of FIG. 4A is for inspecting a reflective device 490. Scan head 400 contains an array of collimating lenses 120 and an array of Fourier transform lenses 130. Each array is arranged as shown in FIG. 2 in columns offset relative to each other in a direction perpendicular to a scanning direction. A concern for scan head 400 is variation in distance between lenses 130 and device 490 that results in a translation of beam position. Accordingly, distance between device under test 490 and scan head 400 must be controlled.

Figure 4B:
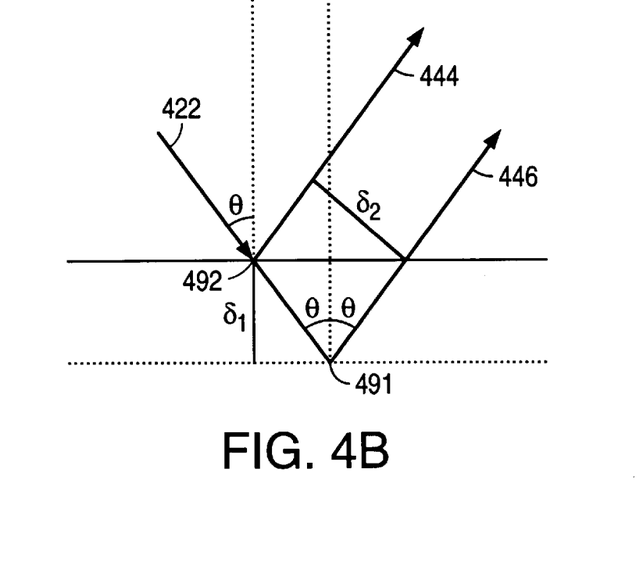
FIG. 4B illustrates Fourier transform light pattern offsets that result in the system of FIG. 4A, from variations in the position of a device under test.

FIG. 4B illustrates that a variation $\delta_1$ in the distance between scan head 400 and DUT 490 results in a translation $\delta_2$ of the intensity pattern of reflected light. In particular, a ray 422, which originates along the axis of collimating lens 120, when reflected from a point 491, becomes a ray 446 which travels along the axis of FT lens 130. However, if device 490 is closer to lenses 120 and 130, a reflected ray 444 is offset from ray 446 and the axis of FT lens 130. Equation 1 gives the translation $\delta_2$ of the beam position as a function of variation $\delta_1$.

$$\delta_2 = 2*\delta_1*\cos\theta*\tan\theta \qquad \text{Equation 1}$$

Setting $\theta=30°$, for example, makes translation $\delta_2$ equal to variation $\delta_1$. The beam translation $\delta_2$ results in a shift $\delta_3$ of the spatial frequency components in the Fourier plane, but shift $\delta_3$ is proportionally reduced according to the focal length of FT lens 130 because Fourier lens are converging lenses. For a 1 mm to 2 mm beam size, small working distance variations of 0.1 mm due, for example, to surface variations in device 490 result in shift in the Fourier plane on the order of 0.05 $\mu$m to 0.1 $\mu$m. Opaque regions of filters 440 can be expanded to block light which has these relatively small offsets. Sensitivity to defects is only slightly reduced by increasing the size of opaque areas in filters 440.

Figure 5:
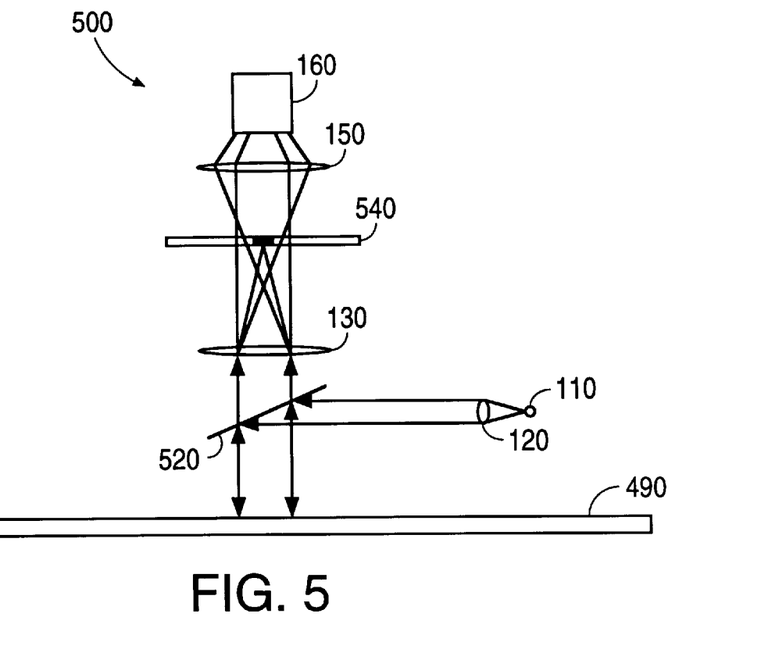
FIG. 5 shows a Fourier transform cell for normal incidence refection.

For normal incidence reflection, angle $\theta$ is 0°, and $\delta_2$ and $\delta_3$ are 0 for all $\delta_1$. FIG. 5 shows a single Fourier transform cell 500 which transforms light reflected at normal incidence. Fourier transform cell 500 includes a beam splitter 520 between collimating lens 120 and device 490. Beam splitters are well known and may be, for example, half-silvered mirrors. Beam splitter 520 reflects light from collimating lens 120 so that the light strikes device 490 at normal incidence and reflects back to beam splitter 520. Beam splitter 520 transmits to FT lens 130 some of the reflected light from device 490. At normal incidence, the Fourier transform pattern has no shift, and opaque regions in spatial filter 540 do not require expansion for shifts.

Figure 6:
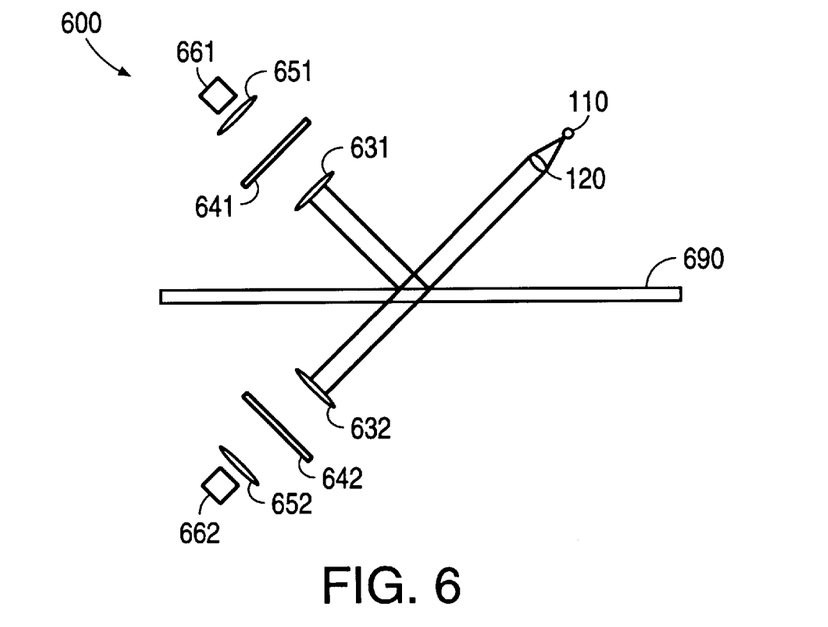
FIG. 6 shows a Fourier transform cell for simultaneous measurements of Fourier transforms of light reflected and transmitted by a device under test.

FIG. 6 illustrates an FT cell 600 which uses both reflected and transmitted light when inspecting a device under test 690. FT cell 600 contains one light source 110 and associated collimating lens 120, but contains two FT lenses 631 and 632, two spatial filters 641 and 642, two sets of collecting optics 651 and 652, and two photodetectors 661 and 662. Spatial filters 641 and 642 will typically have different patterns because the Fourier transform of the reflected light will differ from the Fourier transform of the transmitted light. Multiple cells identical to cell 600 can be arranged in the cell pattern as illustrated previously in FIG. 2 and described above to provide coverage of a scan width of a scan head.

Although the present invention has been described with reference to particular embodiments, the description is only an example of the invention's application and should not be taken as a limitation. In particular, embodiments disclosed illustrate some components as single-lens optical systems. Such components can be replaced by optical systems including multiple lenses, mirrors, holographic elements, and/or other devices which perform the functions disclosed. Various other adaptations and combinations of features of the embodiments disclosed are within the scope of the invention as defined by the following claims.

We claim:

1. An inspection system comprising:

an illumination system which generates a plurality of light beams to illuminate a plurality of separated areas on a device under test;

a first plurality of lenses, each lens being positioned to form a Fourier transform light pattern using light transmitted through a corresponding one of the separated areas;

a first detector system which measures light from the Fourier transform patterns formed by the first plurality of lenses;

a second plurality of lenses, wherein each lens in the second plurality forms a Fourier transform light pattern from light reflected from a corresponding one of the separated areas; and a second detector system which measures light from the Fourier transform light patterns formed by the second plurality of lenses.

2. The system of claim 1, wherein each of the beams is along a normal to a corresponding one of the separate areas on the device under test.

3. The system of claim 1, wherein the lenses in the first plurality are in a one-to-one correspondence with the separate areas.

4. An inspection system comprising:

an illumination system which generates a plurality of light beams to illuminate a plurality of separated areas on a device under test, wherein the illumination system comprises a multiplexed light source which when operating in a first mode illuminates a first set of the separated areas and not a second set of the separated areas and when operating in a second mode illuminates the second set of the separated areas and not the first set of the separated areas;

a plurality of lenses, each lens being positioned to form a Fourier transform light pattern using light from a corresponding one of the separated areas; and a detector system which measures light from the Fourier transform patterns formed by the plurality of lenses.

5. The system of claim 4, wherein the detector system comprises a plurality of photodetectors, each photodetector being optically coupled to measure light from one area in the first set of separated areas and from one area in the second set of separated areas.

6. The system of claim 4, further comprising a mechanism for causing relative motion between the illumination system and the device under test, wherein during the relative motion, the illuminating system switches between operating in the first mode and operating in the second mode.

* * * * *